(12) United States Patent
Isogai et al.

(10) Patent No.: US 7,344,247 B2
(45) Date of Patent: Mar. 18, 2008

(54) OCULAR ACCOMMODATIVE FUNCTION EXAMINATION APPARATUS

(75) Inventors: Naoki Isogai, Nishio (JP); Noriji Kawai, Gamagori (JP); Miwako Hanaki, Toyohashi (JP); Akihiro Hayashi, Toyokawa (JP); Mikio Kurachi, Hazu-gun (JP); Toshiya Kobayashi, Kariya (JP)

(73) Assignee: Nidek Co., Ltd., Gamagori-shi (JP)

( * ) Notice: Subject to any disclaimer, the term of this patent is extended or adjusted under 35 U.S.C. 154(b) by 469 days.

(21) Appl. No.: 10/901,162

(22) Filed: Jul. 29, 2004

(65) Prior Publication Data

US 2005/0041210 A1 Feb. 24, 2005

(30) Foreign Application Priority Data

Jul. 31, 2003 (JP) ............................. 2003-284451
Jul. 31, 2003 (JP) ............................. 2003-284452

(51) Int. Cl.
*A61B 3/10* (2006.01)
(52) U.S. Cl. ....................................... 351/205; 351/211
(58) Field of Classification Search ................ 351/205, 351/206, 208–211, 221
See application file for complete search history.

(56) References Cited

U.S. PATENT DOCUMENTS 5,463,430 A 10/1995 Isogai et al.
2005/0007551 A1* 1/2005 Wakil et al. ................ 351/205

FOREIGN PATENT DOCUMENTS

JP A 2003-70740 3/2003

OTHER PUBLICATIONS

Suzuki et al., "Evaluation of Accommodative Function by High Frequency Component of Accommodative Microfluctuation," Jpn J Vis Sci, vol. 22, pp. 93-97, 2001.

* cited by examiner

*Primary Examiner*—Huy K Mai
(74) *Attorney, Agent, or Firm*—Oliff & Berridge, PLC (57) ABSTRACT

An ocular accommodative function examination apparatus for examining an accommodative function of an examinee's eye, includes: a fixation target presenting optical system which presents a fixation target at a presenting position to the eye, the presenting position being changeable in a direction of a visual axis of the eye; a refractive power measuring optical system which measures refractive power of the eye; an analysis part which acquires variation or fluctuation in the refractive power of the eye gazing at the fixation target at a certain presenting position within a predetermined time based on a result of measurement by the measuring optical system, and determines tho accommodative function of the eye based on the acquired variation or fluctuation; a display part which displays a result determined by the analysis part; and a control part which controls presenting of the fixation target to perform at least one of simple examination for determining the accommodative function with respect to a first presenting position and thorough examination for determining the accommodative function with respect to a second presenting position, the second presenting position including different positions more than the first presenting position.

7 Claims, 8 Drawing Sheets

OCULAR ACCOMMODATIVE FUNCTION EXAMINATION APPARATUS

BACKGROUND OF THE INVENTION

1. Field of the Invention

The present invention relates to an ocular accommodative function examination apparatus for objectively examining an accommodative function of an examinee's eye.

2. Description of Related Art

When refractive power of an eye of an examinee who gazes at a target (optotype) is objectively observed (detected) with time, the refractive power exhibits fluctuation like a sine wave, called accommodative microfluctuation. This accommodative microfluctuation is separated into a high frequency component (1.0-2.3 Hz) and a low frequency component (less than 0.6 Hz). In recent years, attention has been given to that the "frequency of occurrence (spectral power) of the high frequency component" (hereinafter, HFC) of the accommodative microfluctuation has certain correlation with the degree of accommodative constriction (excessive tonic accommodation, accommodative spasm); e.g., the HFC increases as a burden (constriction) on the ciliary muscle becomes larger. Based on this point of view, there has been proposed a method for examining the degree of the accommodative constriction by examining the HFC (see "Evaluation of accommodative function by HFC of accommodative microfluctuation", Visual Science, Vol. 22 No. 3) Because it is thought that accommodation abnormal is one of causes of asthenopia (eyestrain, eye fatigue), knowing the degree of the accommodative constriction is meaningful.

SUMMARY OF THE INVENTION

The present invention has been made in view of the above circumstances and has an object to overcome the above problems and to provide an ocular accommodative function examination apparatus capable of efficiently and precisely examining an accommodative function of an eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ocular accommodative function examination apparatus for examining an accommodative function of an examinee's eye, including: a fixation target presenting optical system which presents a fixation target at a presenting position to the eye, the presenting position being changeable in a direction of a visual axis of the eye; a reactive power measuring optical system which measures refractive power of the eye; an analysis part which acquires variation or fluctuation in the refractive power of the eye gazing at the fixation target at a certain presenting position within a predetermined time based on a result of measurement by the measuring optical system, and determines the accommodative function of the eye based on the acquired variation or fluctuation; a display part which displays a result determined by the analysis part; and a control part which controls presenting of the fixation target to perform at least one of simple examination for determining the accommodative function with respect to a first presenting position and thorough examination for determining the accommodative function with respect to a second presenting position, the second presenting position including different positions more than the first presenting position.

According to another aspect, the present invention provides an ocular accommodative function examination apparatus for examining an accommodative function of an examinee's eye, including: a fixation target presenting optical system which presents a fixation target at a presenting position to the eye, the presenting position being changeable in a direction of a visual axis of the eye; a refractive power measuring optical system which measures refractive power of the eye; an analysis part which acquires variation or fluctuation in the refractive power of the eye gazing at the fixation target at a certain presenting position within a predetermined time based on a result of measurement by the measuring optical system, and determines the accommodative function of the eye based on the acquired variation or fluctuation; a display part which displays a result determined by the analysis part; and a control part which sets a meridian direction, in which the variation or fluctuation in the refractive power is acquired, to a strong principal meridian direction or a weak principal meridian direction of astigmatism.

According to another aspect, the present invention provides an ocular accommodative function examination apparatus for examining an accommodative function of an examinee's eye, including: a fixation target presenting optical system which presents a fixation target at a presenting position to the eye, the presenting position being changeable in a direction of a visual axis of the eye; a refractive power measuring optical system which measures refractive power of the eye; an alignment detecting optical system which detects an alignment state of the measuring optical system with respect to the eye; an analysis part which acquires variation or fluctuation in the refractive power of the eye going at the fixation target at a certain presenting position within a predetermined time based on a result of measurement by the measuring optical system, and determines the accommodative function of the eye based on the acquired variation or fluctuation, the analysis part eliminating the result of the measurement acquired while the alignment state falls outside a predetermined proper state based on a result of detection by the aliment detecting optical system; and a display part which displays a result determined by the analysis part.

Further, according to another aspect, the present invention provides an ocular accommodative function examination apparatus for examining an accommodative function of an examinee's eye, including: a fixation target presenting optical system which presents a fixation target at a presenting position to the eye, the presenting position being changeable in a direction of a visual axis of the eye; a refractive power measuring optical system which measures refractive power of the eye; an analysis part which acquires variation or fluctuation in the refractive power of the eye gazing at the fixation target at a certain presenting position within a predetermined time based on a result of measurement by the measuring optical system, and determines the accommodative function of the eye based on the acquired variation or fluctuation, the analysis part determining which of predetermined plural ranks the determined accommodative function belongs to; and a display part which displays a result determined by the analysis part.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
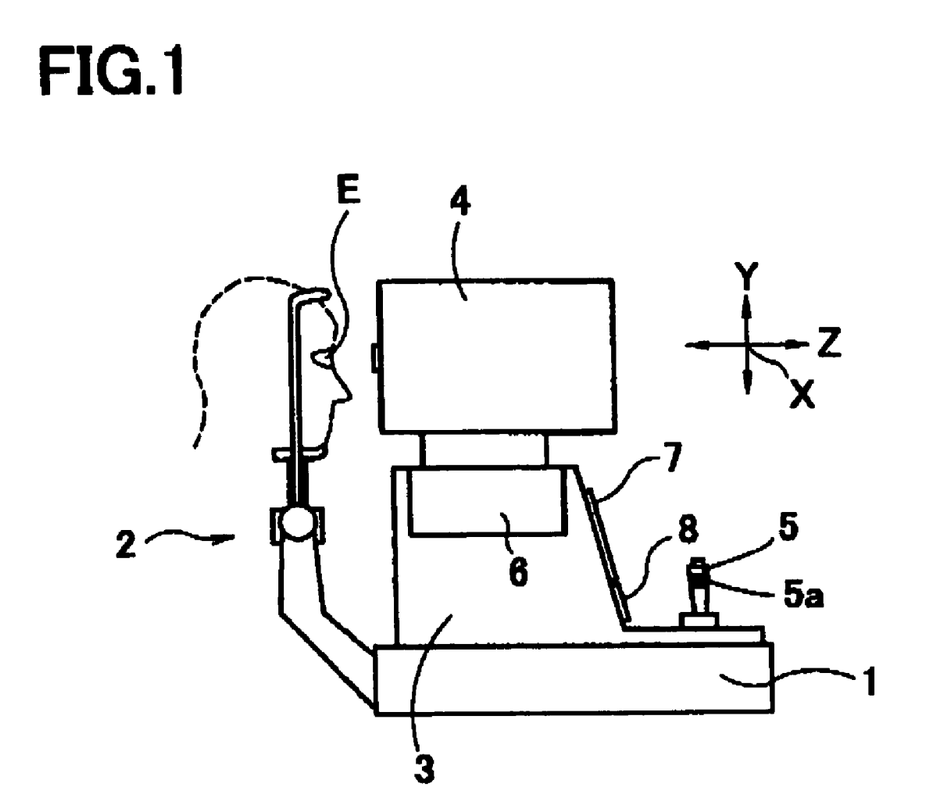
FIG. 1 is a schematic external view of an ocular accommodative function examination apparatus.

A detailed description of a preferred embodiment of an ocular accommodative function examination apparatus embodying the present invention will now be given referring to the accompanying drawings. FIG. 1 is a schematic external view of the ocular accommodative function examination apparatus in the present embodiment. The examination apparatus includes a base 1, a head support unit 2 fixed to the base 1, a movement carriage g which is movably placed on the base 1, and a measurement part 4 which is movably placed on the movement carriage 3 and houses optical systems which will be mentioned later. The measurement part 4 is moved in a rightward/leftward direction (X-direction), an upward/downward direction (Y-direction), and a backward/frontward direction (Z-direction) by a moving part 6 provided in the movement carriage 3. The moving part 6 is constructed of a sliding mechanism and a motor provided for each of the X-, Y-, and Z-directions, and others. The movement carriage 3 is moved on the base 1 in the X- and Z-directions respectively by operation of a joystick 5. Further, the measurement part 4 can be moved in the Y-direction even by operation of a rotary knob 5a. The movement carriage 3 is provided with a monitor 7 which displays an image of an eye E under observation and various information such as examination results, a switch part 8 on which many switches are arranged, and others.

Figure 2:
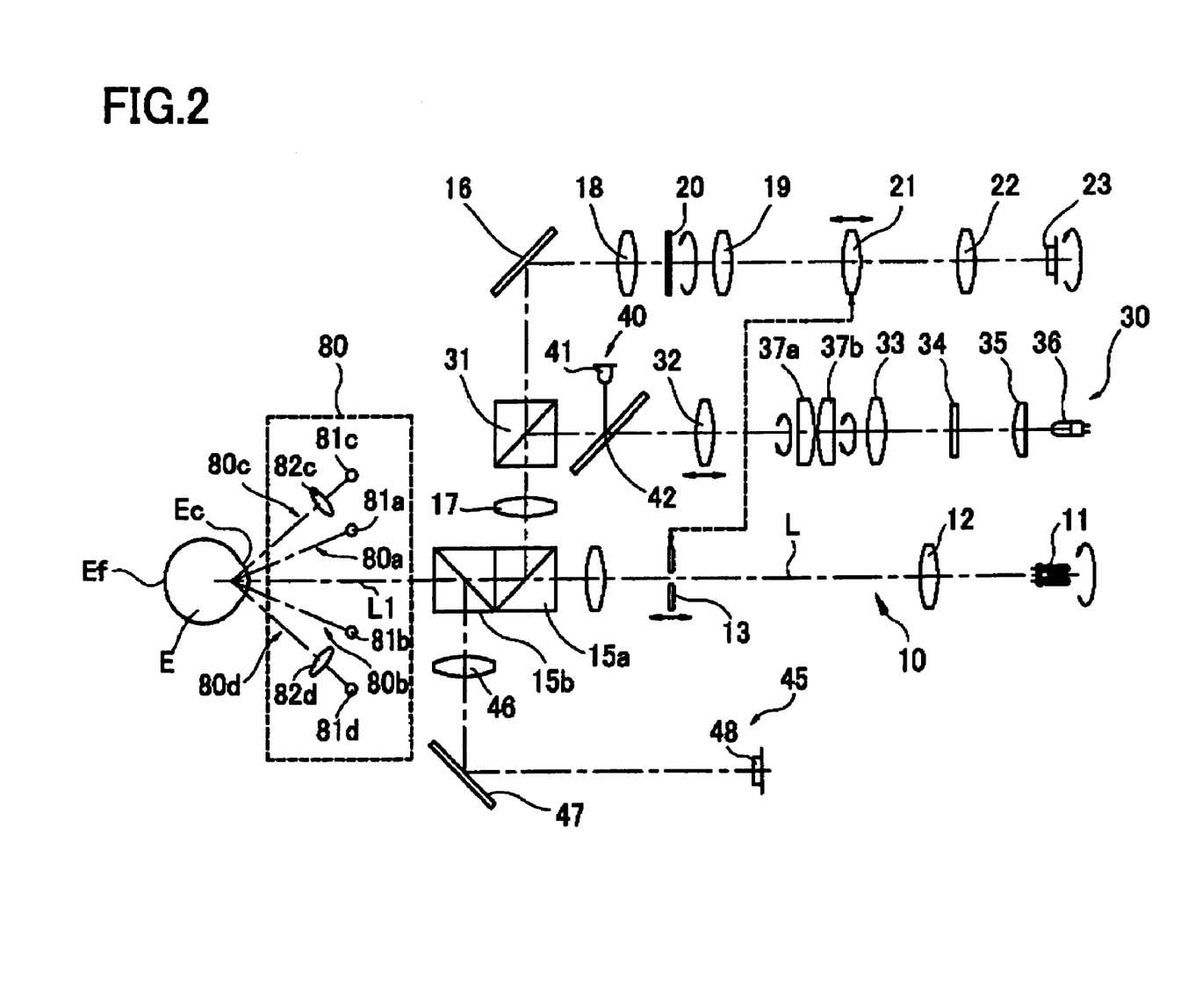
FIG. 2 is a schematic structural diagram of an optical system of the examination apparatus.

FIG. 2 is a schematic structural diagram of optical systems of the examination apparatus, including an eye refractive power measuring optical system 10, a fixation target presenting optical system 30, a first alignment target projecting optical system 40, a second alignment target projecting optical system 80, and an observation optical system 45, which will be mentioned below in detail.

In the eye refractive power measuring optical system 10, infrared examination (measurement) light emitted from two examination (measurement) light sources 11 passes through a condensing lens 12, an examination (measurement) target plate 13, a projection lens 14, and half mirrors 15a and 15b and then is projected to a fundus Ef of the eye E. A reflection light of the examination light from the fundus Ef travels to a light receiving element (photodetector) 23 for examination (measurement) through the half mirror 15b and the half mirror 15a, an objective lens 17, a half mirror 31, a mirror 16, a relay lens 18, a strip-shaped mask 20 for blocking corneal reflection light, a relay lens 19, a movable lens 21, and an image forming lens 22. The light sources 11, the mask 20, and the light receiving element 23 are placed to be synchronously rotatable about an optical axis (path) L. The target plate 13 has a target (a spot opening) for examination (measurement) and is disposed to be moved along the optical axis L to a substantially conjugate position with the fundus Ef. The lens 21 is placed to be moved along the optical axis L together with the target plate 13. The mask 20 is disposed in a substantially conjugate position with a cornea Ec of the eye E. Further, the mask 20 is provided with a light receiving element (photodetector) which the corneal reflection light enters, that is, which receives the corneal reflection light. Based on a signal outputted from this light receiving element, it is detected whether the eye E is blinking or not.

In the fixation target presenting optical system 80, visible light emitted from a light source 36 passes through a condensing lens 35 and illuminates a fixation target (stimulus target) provided on a fixation target plate 34. The fixation target light is projected onto the fundus Ef through a relay lens 33, plus cylindrical lenses 37b and 37a, a relay lens 32, a dichroic mirror 42, the half mirror 31, the lens 17, the half mirrors 15a and 15b in order. The fixation target on the fixation target plate 34, which is commonly used as a fixation target, is positioned at a focal point of the lens 33. The lenses 37a and 37b have an equal focal distance and are disposed to be independently rotatable in the same or opposite direction about the optical axis L. These lenses 37a and 37b constitute an astigmatism correcting optical system. It is to be noted that when two cylindrical lenses are used to produce an astigmatic (cylindrical) component, a spherical component which is produced in association with the generation of the astigmatic component is corrected. The lens 32 is placed to be movable on the optical axis L (its moving distance is proportional to a spherical power of the examinee's eye), thereby optically changing a presenting position (distance) of the fixation target in a direction of the visual axis of the eye E. In the measurement of eye refractive power, the lens 32 is moved to apply a fogging to the eye E in order to relieve (relax the accommodation of the eye E. In an alternative, the change of the presenting position of the fixation target may be made by moving the fixation target plate 34, lens 35, and light source 36 in combination along the optical axis L.

The first alignment target projecting optical system 40 is constructed to project a target to the cornea Ec from a direction along the visual axis of the eye E, the target being used for alignment in the X- and Y-directions. In this optical system 40, infrared alignment light (alignment target) emitted from a point light source 41 is projected onto the cornea Ec from front along the optical axis L by way of the dichroic mirror 42, the half mirror 31, the lens 17, and the half mirrors 15a and 15b in order.

The second alignment target projecting optical system 80 is constructed to project a target to the cornea Ec from an oblique direction with respect to the direction of the visual axis of the eye E, the target being used for alignment in the Z-direction. This optical system 80 includes two first target projecting optical systems 80a and 80b disposed in symmetrical relation with respect to the optical axis L1 and two second target projecting optical systems 80c and 80d disposed outside the first target projecting optical systems 80a and 80b farther away than the optical system 80a and 80b from the optical axis L1) in symmetrical relation with respect to the optical axis L1. Infrared alignment light (alignment target) emitted from point light sources 81*a* and 81*b* of the first target projecting optical systems 80*a* and 80*b* is projected to the cornea Ec (the alignment target is projected at finity). Infrared alignment light (alignment target) emitted from point light sources 81*c* and 81*d* of the second target projecting optical systems 80*c* and 80*d* is projected to the cornea Ec through collimating lenses 82*c* and 82*d* (the alignment target is projected at infinity). The first target projecting optical systems 80*a* and 80*b* are disposed so that their projecting optical axes intersect with the optical axis L at a first predetermined angle. The second target projecting optical systems 80*c* and 80*d* are disposed so that their projecting optical axes intersect with the optical axis L at a second predetermined angle larger than the first predetermined angle.

In the observation optical system 45, an image of an anterior segment of the eye E illuminated by infrared light emitted from an illumination light source not shown and an image of each of the alignment targets projected by the target projecting optical systems 40 and 80 are photographed (picked up) by a CCD camera 48 through the half mirror 15*b*, an objective lens 46, and a mirror 47.

Figure 3:
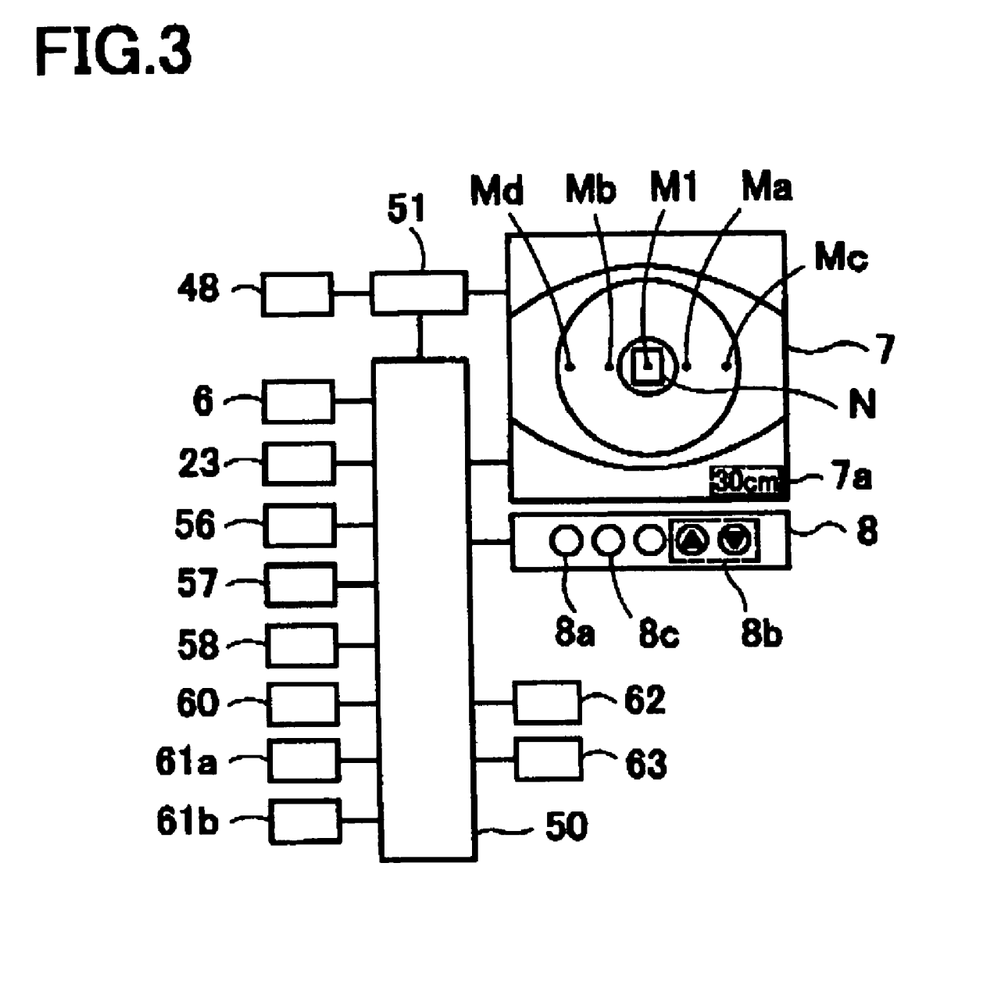
FIG. 3 is a schematic structural diagram of a control system of the examination apparatus.

FIG. 3 is a schematic structural diagram of a control system of the examination apparatus. An image signal from the camera 48 is inputted to an image processing part 51 and is outputted to (displayed on) the monitor 7. To an analysis and control part 50, connected are the moving part 6, the monitor 7, the image processing part 51, the switch part 8, the light receiving element 23, a motor 56 for rotating the light sources 11, the mask 20 and the light receiving element 23, a motor 57 for moving the target plate 13 and the lens 21, a potentiometer 60 for detecting a moved position of the target plate 13 (or the lens 21), a motor 58 for moving the lens 32, a motor 61*a* for rotating the lens 37*a*, a motor 61*b* for rotating the lens 37*b*, a memory 62, a sound generator 63, and others. The analysis and control part 50 controls the above components and also determines eye refractive power based on output signals of the light receiving element 23 and the potentiometer 60 and further determines an accommodative function.

The operation of the apparatus constructed as above is explained below At first, objective measurement of refractive power for distance (far vision, far eight) (hereinafter, distance refractive power) is described. Before starting the measurement of distance refractive power, a mode selection switch 8*a* of the switch part 8 is operated to select a distance refractive power measurement mode. Then, an examiner requests an examinee to rest his head on the head support unit 2 and makes alignment of the measuring optical system 10 with respect to the eye E. This embodiment exemplifies the case where an automatic alignment mode and an automatic tracking mode are selected.

Figure 8:
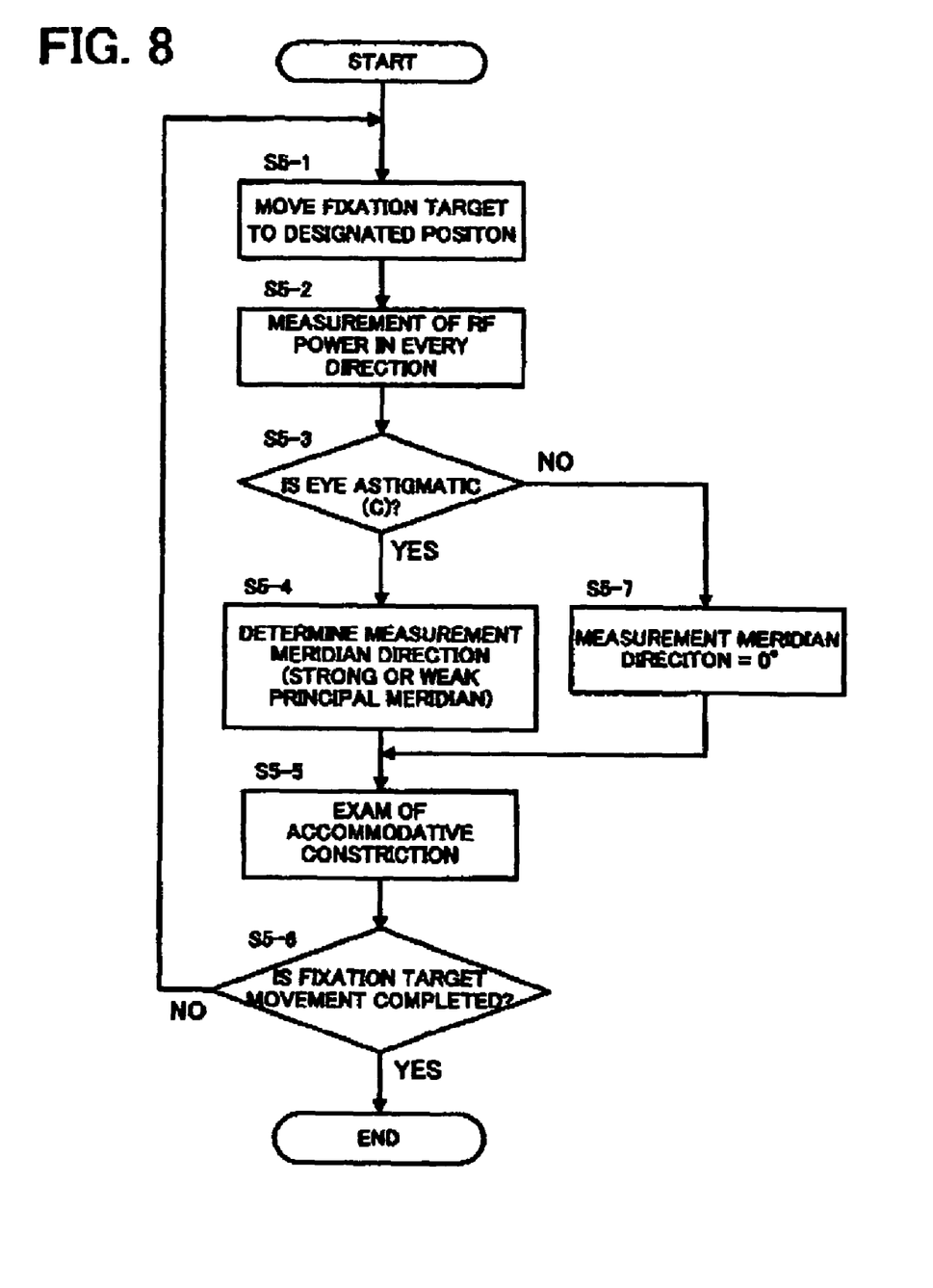
FIG. 8 is a flowchart to explain a measuring method for reducing errors in measuring an eye of an examinee with astigmatism.

While observing an image of an anterior segment of the eye E and a reticle N both displayed on the monitor 7, the examiner operates the joystick 5 and the rotary knob 5*a* to move the movement carriage 3 and the measurement part 4 in the X-, Y-, and Z-directions for rough alignments As shown in FIG. 8, when an alignment target image M1 generated by means of the target projecting optical system 40 and four alignment target images Ma to Md generated by means of the target projecting optical system 80 appear on the monitor 7, the automatic alignment and the automatic tracking are performed. The target image M1 and the target images Ma to Md are photographed by the camera 48 and are detected and processed in the image processing part 51. The analysis and control part 50 determines whether an alignment state in the X- and Y-directions is proper based on a result of the detection of the centered target image M1. Further, the analysis and control part 50 determines whether an alignment state in the Z-direction is proper based on results of the detection of the target images Ma to Md.

The determination of the alignment state in the Z-direction is executed by a comparison between an image distance between the infinit target images Mc and Md generated by the second target projecting optical systems 80*c* and 80*d* and an image distance between the finit target images Ma and Mb generated by the first target projecting optical systems 80*a* and 80*b*. In the case of projection of a target at infinit, an image distance (image height) of the target image substantially remains unchanged even when a working distance (a distance in the Z-direction) in changed. In the case of projection of a target at finit, on the other hand, an image distance (image height) of the target image changes according to changes in working distance. This characteristics may be utilized to determine an alignment state in the Z-direction (see U.S. Pat. No. 5,463,430 corresponding to Japanese unexamined patent publication No. Hei 6-46999).

The analysis and control part 50 drivingly controls the moving part 6 based on results of the determination of the alignment states in the X-, Y-, and Z-directions to move the measurement part 4 in respective directions. When all of the alignment states in the above directions fall within a predetermined allowable range (proper range), the analysis and control part 50 automatically generates a trigger signal to start measurement.

The examination light from the light sources 11 is converged to a point near the cornea Ec and reaches the fundus Ef. If the eye E is normal, an image of the examination target (light) reflected by the eye E is formed on the light receiving element 23. If the eye E has abnormal refractive power (refractive error), the analysis and control part 50 drives the motor 57 based on an output signal from the light receiving element 23 to move the target plate 13 and the lens 21 to a substantially conjugate position with the fundus Ef.

Next, the analysis and control part 50 drives the motor 58 to move the lens 32, thereby bringing the fixation target plate 34 to a substantially conjugate position with the fundus Ef, and thereafter move the lens 32 again so that a fogging is applied by an appropriate diopter to relieve (relax) the accommodation of the eye E. In this state where the eye E is fogged, the analysis and control part 50 drives the motor 56 to rotate the light sources 11, the mask 20 and the light receiving element 23, 180° about the optical axis L. During rotation, the analysis and control part 50 drives the motor 57 based on an output signal from the light receiving element 23 to move the target plate 13 and the lens 21. Based on results of the detection of a distance (amount) of movement of the target plate 13 or the lens 21 by the potentiometer 60, the analysis and control part 50 determines refractive power in each meridian direction. The analysis and control part 50 applies predetermined processing to this refractive power to determine each of refractive power values S(spherical power), C(cylindrical power), and A(astigmatic axis angle). The determined refractive power is values S, C, and A in a nonaccommodative state (fogged state) are stored in the memory 62.

Figure 4:
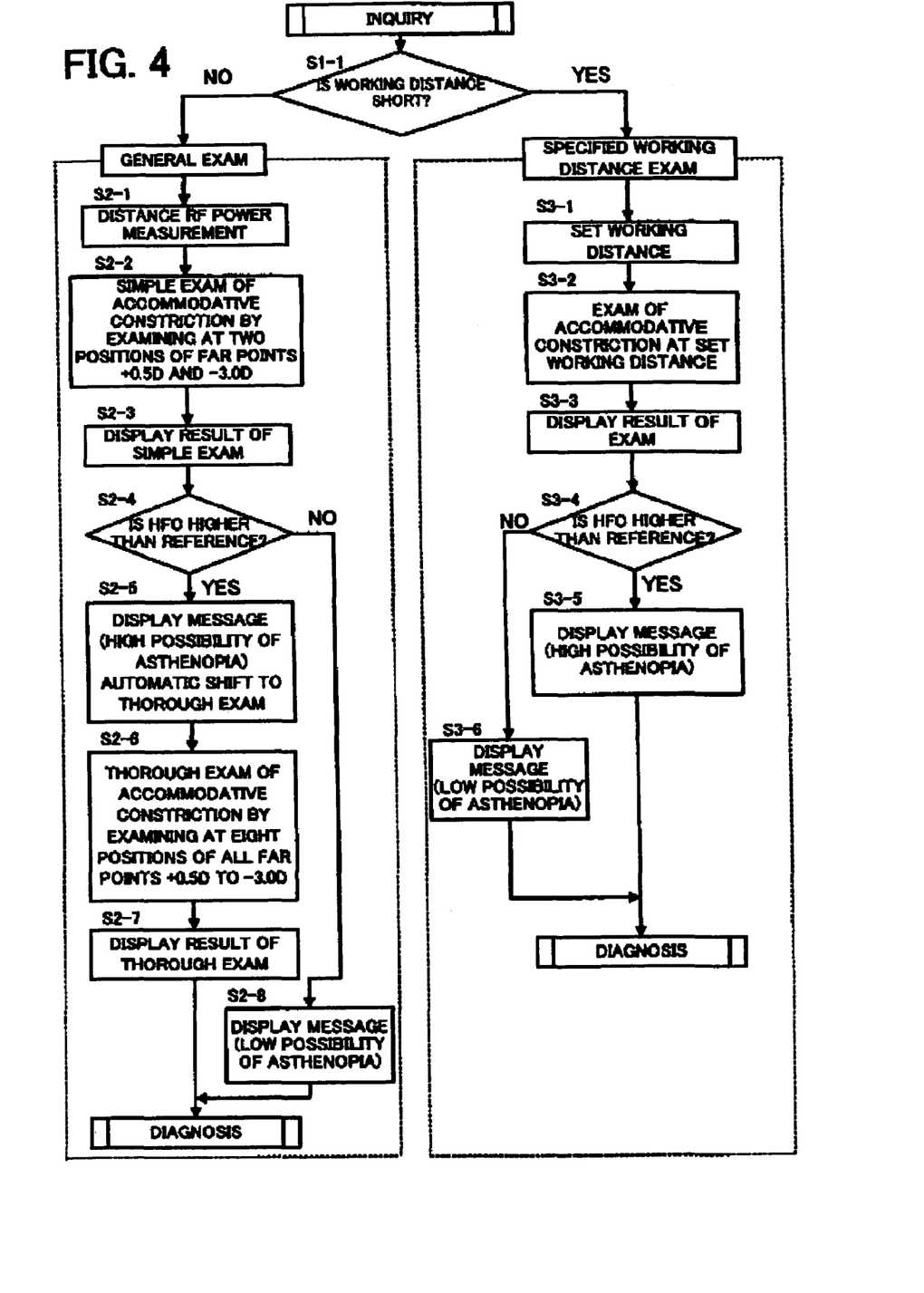
FIG. 4 is a flowchart to explain examination of accommodative constriction.

Next, examination of accommodative constriction is explained referring to FIG. 4. Regarding the accommodative constriction examination, there are prepared a general examination mode and a specified working distance examination mode. The examiner operates the mode selection switch 8*a* based on information on inquiry to the examines to select between the general examination mode and the specified working distance examination mode (step 1-1).

<General Examination>

For the general examination mode, there are provided a thorough examination mode and a simple examination mode. The thorough examination mode is to determine an accommodative constriction state by changing a presenting position of a fixation target to eight positions in turn in steps of a predetermined diopter (e.g., 0.5D) on the basis of the position of an S value (which can be regarded as a far point of the eye E) of distance refractive power in the aforesaid nonaccommodative state, and acquiring variation (fluctuation) in refractive power within a predetermined time T (e.g., 20 seconds) at each presenting position. On the other hand, the simple examination mode is to determine an accommodative constriction state in a simple manner that extracts moving positions (presenting positions) of a fixation target from those in the thorough examination mode, thereby reducing the number of moving positions.

When the general examination mode is selected, the distance refractive power examination is executed in the nonaccommodative state (step 2-1) in the same manner as above, and then the simple examination mode is fist established (step 2-2). In the simple examination, as a major presenting position of a fixation target which burdens the eye E with accommodation, for example, the fixation target is moved to two positions for +0.5D and −3.0D on the basis of the position corresponding to an S value of distance refractive power. Then, variations in refractive power within the time T at each presenting position are acquired. The acquired variations in refractive power are stored in the memory 62 in one-to-one correspondence with the presenting positions. Based on an output signal of the light receiving element of the mask 20 disposed in the substantially conjugate position with the cornea Ec, further, it is detected whether or not the eye E is blinking while the variations in refractive power are acquired. Data acquired when the blinking is detected is checked to avoid the use of the data during later calculation of the HFC.

It is to be noted that the fixation target presenting position in the simple examination mode can be set arbitrarily with the switches 8b and 8c of the switch part 8. By operation of the switch 8c, the monitor 7 is caused to display a screen for setting (selecting) a fixation target presenting position to be used in the simple examination mode. The switch 8b is then operated to set (select) the fixation target presenting position on the screen. When the switch 8c is operated again, the set information on the fixation target presenting position is updated.

The analysis and control part 50 calculates the HFC based on the variations in refractive power stored in the memory 62. This calculation of HFC is simply explained below. At first, the data checked at the time of detection of blinking of the eye E is removed from the data to be analyzed. Data lose and irregularity due to the blinking are corrected by cubic spline. Then, a frequency analysis is performed by means of a fast Fourier transform (FFT) to calculate a power spectrum (spectral power). This calculation of a power spectrum is conducted at each of intervals set within the time T (20 seconds). Within the time T, the intervals are set to lag behind preceding ones by a predetermined time (e.g., 1 second) and have an equal duration (e.g., 8 seconds). The calculated power spectrum is converted to common logarithms and analyzed. Based on this power spectrum, a mean power spectrum (in dB) in the intervals for high frequency components of 1.0 to 2.3 Hz is determined and evaluated as the "frequency of occurrence of high frequency component" (HFC) of accommodative microfluctuation.

Figure 5:
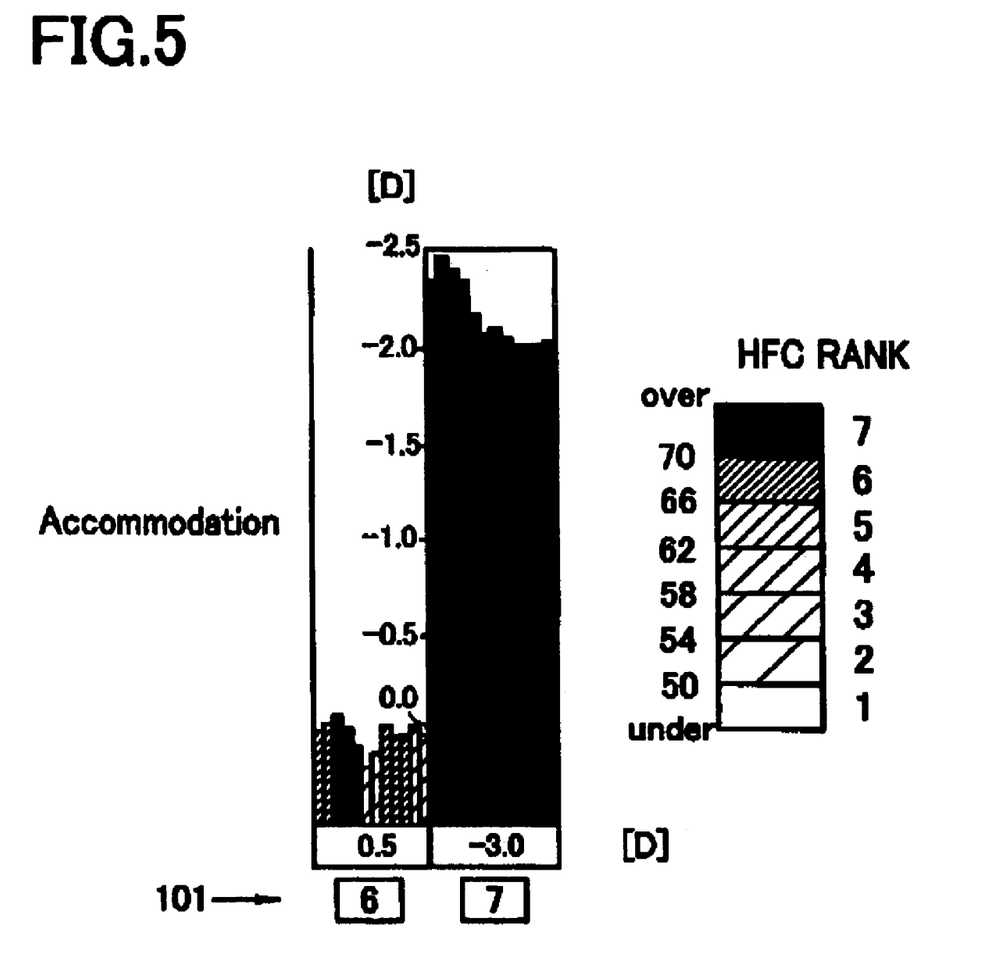
FIG. 5 is an example of a display showing results of examination in a simple examination mode.

Once the HFC is calculated, results of the examination of accommodative constriction is displayed on the monitor 7 (step 2-3). FIG. 5 is an example of a display showing results of examination in the simple examination mode. These examination results are displayed in terms of three parameters; fixation target presenting position, amount of accommodation response (range of accommodation), and HFC, in the form of a three dimensional graph with color cord maps. In this graph, the vertical axis indicates the amount of accommodation response (refractive power D) and the horizontal axis indicates the fixation target presenting position, where variations in the amount of accommodation response corresponding to elapsed times within the time T at each presenting position are graphed in a bar graph. The HFC is color-coded in for example seven levels. For example, an HFC less than 50 is displayed in green, an HFC not less than 70 is displayed in red, and other HFC therebetween is displayed with gradations in color between green through yellow to red. The HFC for a distant target is lower in the eyes with less accommodative constriction, which is expressed in green in the color cord map. The HFC is totally higher in the eyes with much accommodative constriction, which is expressed in red in the color cord map. This shows that the ciliary muscle is in a constricted state.

Next, it is determined whether or not the HFC detected in the simple examination mode is higher than a predetermined reference value (step 2-4). The analysis and control part 50 calculates a mean value of the HFC within the time T at each fixation target presenting position for +0.5D and −3.0D respectively and determines which of seven ranks No. 1 to 7 the mean value belongs to. If it is determined that the HFC belongs to a rank No. 4 or higher (the mean HFC is 58 or more), which indicates that the possibility of asthenopia is high, the monitor 7 displays a message that the mode is shifted to the thorough examination mode for performing detailed examination (step 2-5). Then, the thorough examination is executed (step 2-6). In the thorough examination, on the basis of the position corresponding to the S value of the distance refractive power, the fixation target is moved in turn to eight positions; +0.5D, 0.0D, −0.5D, −1.0D, −1.5D, −2.0D, −2.5D, and −3.0D. Variations in refractive power within the time T at each presenting position is acquired. The acquired variations in refractive power are stored in the memory 62 in one-to-one correspondence with the presenting positions. The HFC is calculated at each of the fixation target presenting positions in the same manner as above and then results of the examination are displayed (step 2-7).

Figure 6:
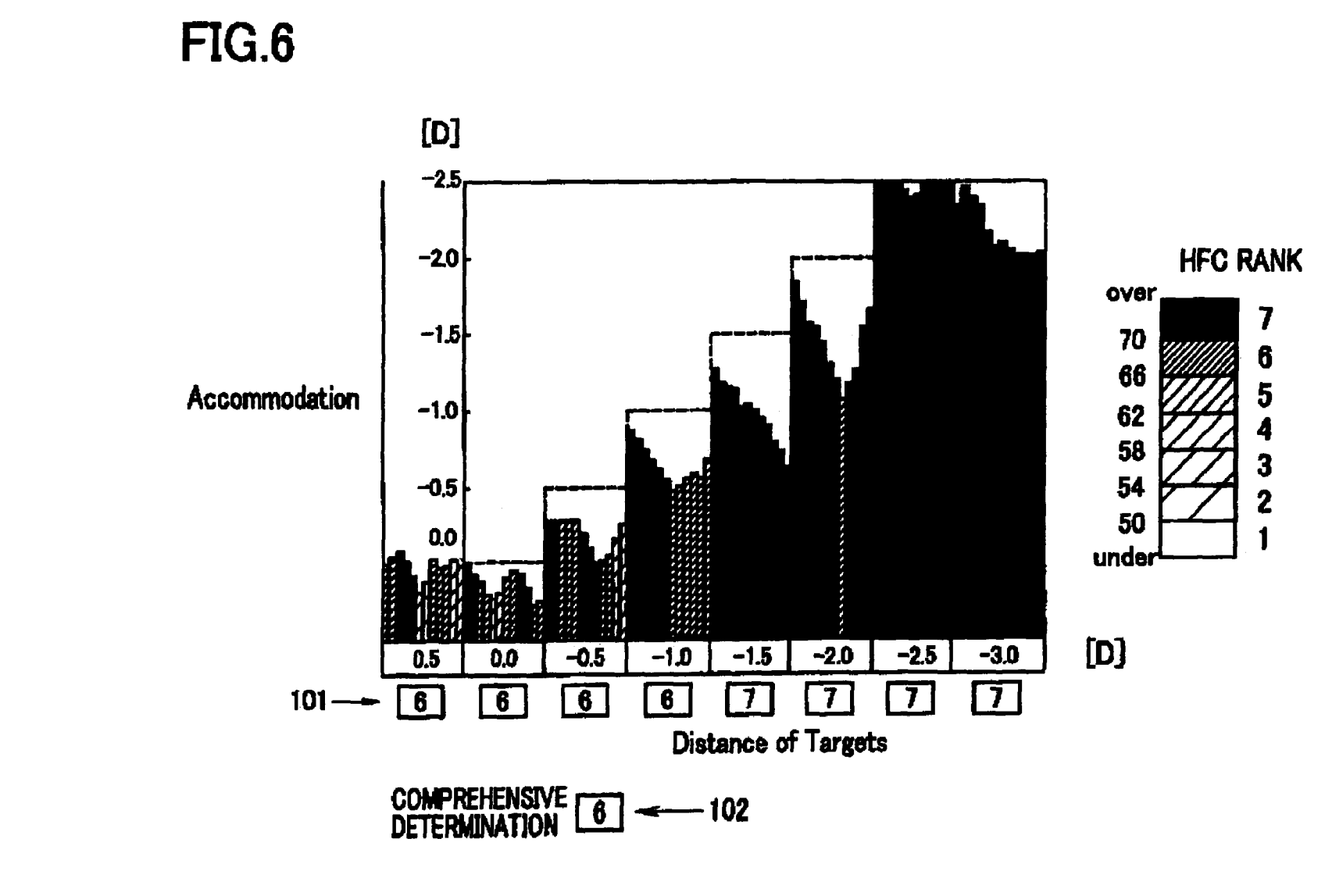
FIG. 6 is an example of a display showing results of examination in a thorough examination mode.

FIG. 6 is an example of a display showing the results of the examination in the thorough examination mode. As in the simple examination mode, the examination results are displayed in terms of three parameters; fixation target presenting position, amount of accommodation response (range of accommodation), and HFC, in the form of a three dimensional graph with color cord maps.

It is to be noted that experience is required to interpret the three dimensional graph. Accordingly, a rank index 101 which represents the degree of accommodative constriction is calculated at each fixation target presenting position and displayed. A value of this rank index 101 is decided in such a manner that the analysis and control part 50 determines a mean of the HFC at each fixation target presenting position and determines which of seven ranks No. 1 to 7 the mean value belongs to, as with the above color-coding. In this embodiment, the constriction degree for each fixation target presenting position of +0.5D, 0.0D, −0.5D, and −1.0D is determined at a rank No. 6. The constriction degree for each fixation target presenting position of −1.5D, −2.0D, −2.5D, and −3.0D is judged as belonging to a rank No. 7. It is to be noted that the ranking in the present embodiment is quantitatively indicated by numerals, but it may be expressed by the number of star marks or the length of bar graphs. Further, the rank index 101 is also displayed in the results of the examination in the simple examination mode.

In the thorough examination mode, in addition to the rank index 101 for each fixation target presenting position, a rank index 102 for results of an examination at all of the fixation target presenting positions is displayed as a comprehensive determination. This rank index 102 is decided in such a manner that the analysis and control part 50 determines a mean of the HFC for all of the fixation target presenting positions and determines which of seven ranks No. 1 to 7 it belongs to. In this embodiment, it is determined that the mean belongs to a rank No. 6, which shows that the degree of accommodative constriction is high.

The quantified rank index 101 or 102 makes it more easy to read the examination results to reduce errors in diagnosis such as decision of cases, decision of courses of treatment, decision of lens prescriptions, etc. A burden on the examinee can also be reduced.

On the other hand, if the HFC is judged as belonging to a rank No. 3 or lower (a mean HFC is less than 58) in step 2-4, the monitor 7 displays a message that the possibility of asthenopia is low(step 2-8), and the examination is terminated. Regarding whether the possibility of asthenopia is high or low, it can be judged from results of the simple examination even without executing the thorough examination. Thus, the examination time (duration) can be significantly shortened and hence the simple examination is useful in screening or the like.

The simple examination mode and the thorough examination mode may be selected individually with the mode selection switch 8a. With the switch 8a, specifically, the simple examination mode is switched to the thorough examination mode when requested after the end of the simple examination with the determination result that the HFC belongs to the rank No. 3 or lower in step 2-4.

<Specified Working Distance Examination>

An explanation is given to the case where a specified working distance examination mode is selected with the mode selection switch 8a. The examination mode is effective in examining an examinee whose principal working distance is short. Based on information of inquiry to the examinee, the examiner sets (selects) the principal working distance (e.g., 30 cm) with the switch 8b. Accordingly, a fixation target is moved to a position corresponding to the set working distance. The set working distance is displayed on the monitor 7 in a working distance box 7a (see FIG. 3). When alignment is made with respect to the eye E and the alignment state falls within the permissible range, the examination of accommodative constriction is automatically executed (step 3-2). The examinee (eye E) is requested to gaze at the fixation target disposed at a presenting position corresponding to the working distance, so that the eye E is burdened with accommodation. Under this burden of accommodation, variations in refractive power within the time T are determined and stored in the memory 62 in one-to-one correspondence with the presenting positions.

When the HFC is calculated based on the acquired variation in refractive power, the monitor 7 display results of the examination of accommodative constriction (step 3-3). The examination results are displayed in the same manner as in FIGS. 5 and 6 in terms of three parameters; fixation target presenting position, amount of accommodation response range of accommodation), and HFC, in the from of a three dimensional graph with color cord maps. Then, it is determined whether the calculated HFC is higher than a reference value (step 3-4). The determination is conducted based on which of seven ranks No. 1 to 7 a mean value of the HFC within the time T belongs to. If it is determined that the mean value belongs to a rank No. 4 or higher (the mean HFC is 58 or more), considering the HFC as being high, the monitor 7 displays a message that the possibility of asthenopia is high and a message to promote a prescription of an additional power lens (step 3-5). If it is determined that the mean value is a rank No. 3 or lower, considering the HFC as being low, the monitor 7 displays a message that the possibility of asthenopia is low (step 3-6).

With the use of the specific working distance examination mode in the above way, it is possible to evaluate whether the examinee is burdened with accommodative constriction at tho examinee's major working distance even without performing the thorough examination of the former general examination mode. This makes it achieve a large reduction of examination time, thereby reducing the burden on the examinee and the examiner.

The examination time in the thorough examination mode can be reduced by the use of the simple examination mode and the specific working distance examination mode as above. Further, in an alternative, another method may be used to shorten the examination time. This method will be explained below with reference to a flowchart of FIG. 7.

Figure 7:
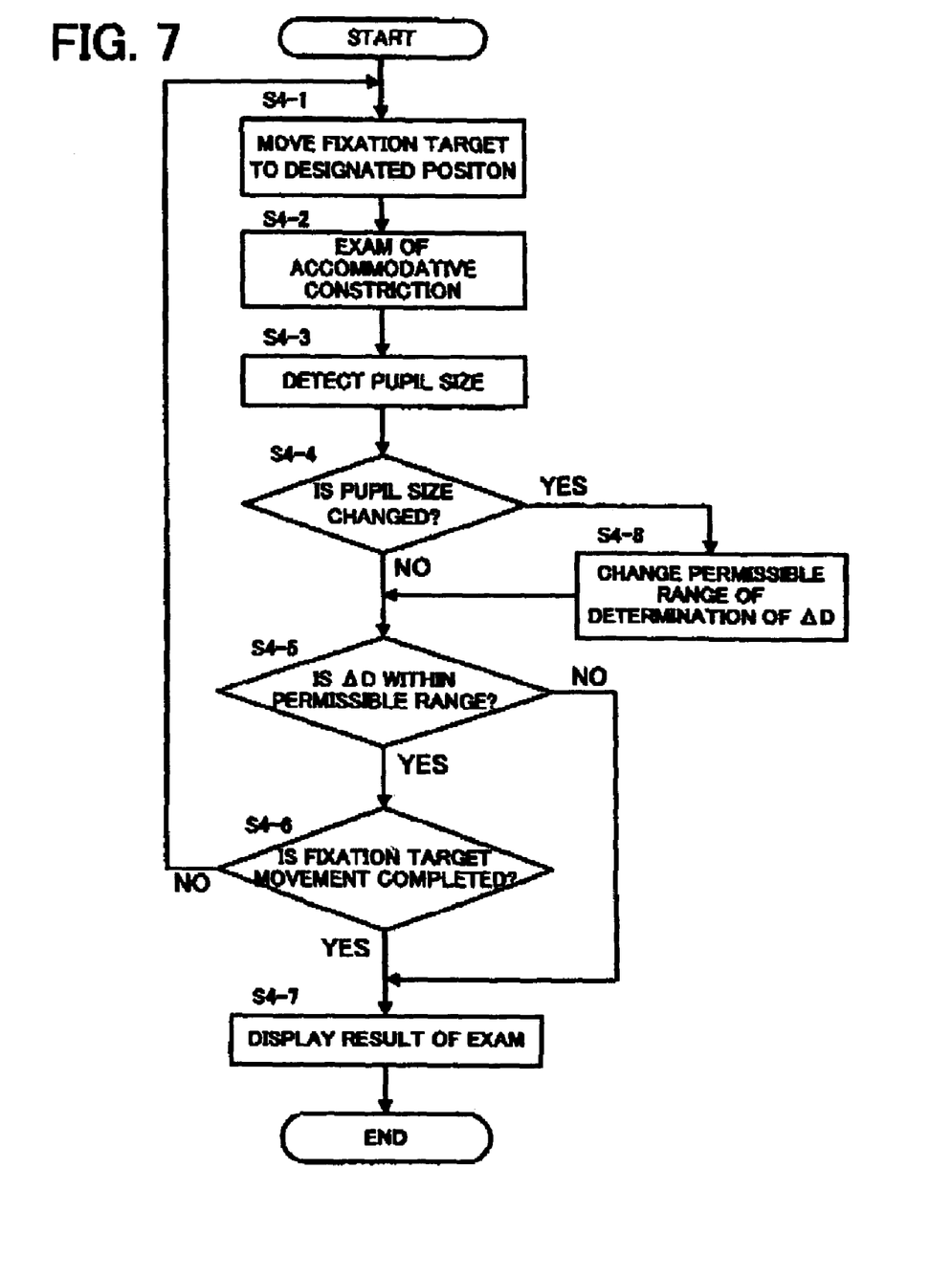
FIG. 7 is a flowchart to explain another example for the purpose of shortening examination time (duration)

At first, a fixation target is moved to a designated position (step 4-1) and an examination of accommodative constriction is executed by presenting the fixation target at that position (step 4-2). In this examination, a pupil size of the eye E is detected (step 4-3). Detecting the pupil size is made by the image processing part 51 based on an image signal representing an anterior segment image from the camera 48. Then, it is determined whether the pupil size is largely changed or not as compared with a size during initial distance refractive power measurement or immediately preceding examination of accommodative constriction (step 4-4). If an amount of change in pupil size is small (for example, if the amount of change is within 1.0 mm), successively, it is determined whether or not a difference ΔD between converted refractive power for the fixation target presenting position and the measured refractive power is within a predetermined permissible range (e.g., within 1.5D) (step 4-5). If ΔD exceeds the permissible range, it indicates that the accommodation of the eye E does not follow (or the eye E fails to accommodate) even when the fixation target presenting position is changed (moved) to a closer position. In this case, it can be determined that the accommodative constriction state unlikely changes. If ΔD exceeds the permissible range, hence, results of the examination are displayed on the monitor 7 at this time and the examination is terminated (step 4-7). This makes it possible to avoid unnecessary examination, thus shortening the examination time. If ΔD is within the permissible range, the fixation target is moved to a next presenting position depending on an answer to whether movement of the fixation target is finished or not (step 4-6), and the examination is continued. In the thorough examination mode exemplified above, eight fixation target presenting positions are set.

When the fixation target presenting position is changed to a closer one, a change in pupil size, namely, miosis may be caused. In the case where significant miosis is detected in step 4-4, it is considered that a focal depth becomes deeper and therefore a factor of improvement of refractive power occurs. A determination condition for termination of the examination in step 4-5 is changed (step 4-8). For example, the permissible range is widened from 1.5D to 2.5D.

It is to be noted that a following state of the accommodation may be determined based on, except for the above condition, whether the refractive power at the current step (a current fixation target presenting position) is larger in a minus direction than the refractive power at a preceding step (an immediately preceding fixation target presenting position) or based on this condition in addition to the aforementioned condition.

If ΔD exceeds the permissible range in the above step 4-5, as in the same manner in the aforementioned simple examination mode, the HFC is calculated and a step may be added to determine whether or not the examination is terminated based on the calculation result. Specifically, the examination is continued if the HFC is a high value (the rank No. 4 or higher), whereas it is terminated if the HFC is a low value (the rank No. 3 or lower). This is because accommodative constriction likely appears in association with the movement of a fixation target to a closer position even when the accommodation of the eye E does not follow the change of a fixation target presenting position.

In the above accommodative constriction examination, the time T during which the variation in refractive power is acquired is not limited to 20 seconds mentioned above maybe changed according to the amount of data needed for a calculation of the HFC. For instance, if a target for the calculation of the high frequency component of accommodative microfluctuation is set at 0.5 Hz or more, the time T is set at about 10 seconds. During this time T, data of live periods or more can be acquired, which is sufficient for the calculation of the HFC. By shortening the time T, it is possible to largely reduce the total examination time. Setting (changing) of the time T is conducted by operation of the switch 8b on the setting (changing) screen which appears on the monitor 7 when the switch 8c is operated.

The interval during which variations in refractive power are acquired may be changed according to the target for the calculation of the high frequency component of accommodative microfluctuation. For example, relative to a high frequency component of up to 2.3 Hz, the variations in refractive power are acquired at intervals of about 80 msec. This means that five variations are acquired during one period of 2.3 Hz, which allows the calculation of the HFC. If a higher frequency component is targeted, it is preferable to acquire variations in refractive power at shorter intervals. The present apparatus allows acquiring of variations in refractive power at intervals of 20 msec by acquiring the variations in refractive power in a certain meridian direction at each fixation target presenting position. To give weight to examination precision, the intervals of acquiring of the variations in refractive power are set at 20 msec. In this case of 20 msec, it also becomes possible to acquire high frequency components of up to 10 Hz. The monitor 7 displays the screen for setting (changing) the intervals of the acquisition by operation of the switch 8c, and setting (changing) of the interval of the acquisition is made to set (change) desired intervals of the acquisition in a range of 80 msec to 20 msec by operation of the switch 8b. As the intervals of the acquisition are set shorter, the amount of data increases, which needs much time for data transfer and data processing. Accordingly, the intervals may be changed to be largish if the total examination time is given importance.

According to the method for acquiring the variations in refractive power in a certain meridian direction as above, errors are caused in results of the measurement of refractive power in a axed meridian direction due to fixation microfluctuation and eye rotation (torsion) if the eye is astigmatic. A measurement method for reducing such errors of measurement is explained using a flowchart of FIG. 8.

At first, a fixation target is moved to a designated position (step 5-1) and then measurement of refractive power in every direction is executed (step 5-2). In this measurement, it is determined whether or not the eye is astigmatic (step 5-3). If the eye is astigmatic, the measurement meridian direction is set to a strong principal meridian direction or a weak principal meridian direction of astigmatism (step 5-4). Assuming that the refractive power is measured in a meridian direction displaced by 45° from the strong or weak principal meridian direction, an angle displacement resulting from the fixation microfluctuation and eye rotation (torsion) likely have a large influence on the measurement of refractive power. On the other hand, when the measurement meridian direction is set to the strong or weak principal meridian direction of astigmatism, there is little influence on tho measurement of refractive power, thereby reducing errors of measurement. The accommodative constriction examination for acquiring variations in refractive power within the time T in the selected measurement meridian direction is executed (step 5-5). This process is repeated until the examination is finished at every fixation target presenting position (step 5-6).

Detection of astigmatism may utilize the results of the measurement of distance refractive power in an initial nonaccommodative state. In some eyes, however, an axial angle of astigmatism may change when the amount of accommodation burdened on the eye is changed. Accordingly, it is preferable to perform refractive power measurement in every direction whenever the fixation target presenting position is shifted and accommodative constriction examination is conducted after decision of the measurement meridian direction. If the eye is not astigmatic, the measurement meridian direction is set to a horizontal direction (0°-direction) (step 5-7).

If astigmatism is found as a result of the initial measurement of distance refractive power or a result of the measurement at each fixation target presenting position, the lenses 37a and 37b are rotated by driving of the motors 61a and 61b, thereby producing cylindrical power for correcting a C value and an A value in the measurement results. When the astigmatic state is corrected, the eye E can stably view the fixation target regardless of the axial angle and the influence of astigmatism on the examination results can be reduced.

In the above accommodative constriction examination, it is convenient to set an automatic tracking mode in addition to an automatic alignment mode. In particular, because the examination time is as long as about three minutes in the thorough examination mode, the use of the automatic tracking mode is effective. In the automatic tracking mode, as in the distance refractive power measurement explained above, the alignment target image M1 generated by the target projecting optical system 40 and the four alignment target images Ma to Md generated by the target projecting optical system 80 are detected and processed by the image processing part 51. Based on the results of detection, the alignment state in each of the X-, Y-, and Z-directions is determined. The measurement part 4 is moved by means of the moving part 6 so that the alignment state in each direction falls within a predetermined permissible range (a proper range).

If the eye moves during the time T during which the variations in refractive power are acquired such that the alignment state falls outside the range, the data acquired in that time is eliminated from the target for the calculation of the HFC. In order to prevent data lose in the time T, the analysis and control part 50 may measure the time corresponding to the eliminated date and continue the acquisition until the total time during which data in the proper alignment state is acquired reaches the time T. According to this manner, it is possible to eliminate the data of low reliability and acquire the results of the measurement with reduced errors. It is also possible to detect blinking of the eye E during the acquisition based on the results of the detection of the alignment target images M1, Ma to Md. If the eye is blinking, the target images M1, Ma to Md cannot be detected as expected. In this case, accordingly, it is detected that the eye was blinking. The data acquired when the blinking is detected is also eliminated from the target for the calculation of the HFC.

Before moving the fixation target to a next designated position a five-minute intermission is taken. During this, the examinee is allowed to blink for resting his eye. Accordingly, consideration needs be given to possibilities that the examines takes his head off the head support unit 2 or moves his eyes largely. The apparatus therefore may be controlled to stop the automatic tracking during the intermission. This makes it possible to reduce unnecessary movement and malfunction of the measurement part 4.

During the time T during which the variations in refractive power are acquired in the proper alignment state, the sound generator 63 is caused to produce a continuous sound or a short-periodic intermittent sound to announce that the variations in refractive power are being acquired to the examiner and the examines. During the five-minute intermission during which the fixation target is moved to a next presenting position, the sound generator 63 is stopped producing a sound or caused to produce a different sound from above, thereby announcing to that effect to the examiner and the examinee. If the alignment state falls outside the permissible range or the variations in refractive power are not acquired normally because the eye E largely moves or due to other reasons, the examiner and the examinee can know to that effect by the sound and thus smoothly perform the examinations.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An ocular accommodative function examination apparatus for examining an accommodative function of an examinee's eye, including:
   a fixation target presenting optical system which presents a fixation target to the eye by changing an optical distance;
   a refractive power measuring optical system which measures refractive power of the eye;
   an analysis part which acquires variation with time of the refractive power of the eye gazing at the fixation target at a certain presenting position within a predetermined time based on a result of measurement by the measuring optical system, and performs a frequency analysis of the acquired variation to determine spectral power of high frequency component of accommodative microfluctuation of the eye; and
   a control part which controls presenting of the fixation target to perform at least one of simple examination in which the fixation target is presented at each of a plurality of different first presenting positions and thorough examination in which the fixation target is presented at each of a plurality of different second presenting positions, the second presenting positions including different positions more than the first presenting positions;
   the analysis part being adapted to determine the spectral power of high frequency component of accommodative microfluctuation of the eye at each of the presenting positions.

2. The ocular accommodative function examination apparatus according to claim 1, wherein the control part controls the presenting of the fixation target to continuously perform the thorough examination when a result of the simple examination exceeds a predetermined reference.

3. An ocular accommodative function examination apparatus for examining an accommodative function of an examinee's eye, including:
   a fixation target presenting optical system which presents a fixation target to the eye by changing an optical distance;
   a refractive power measuring optical system which measures refractive power of the eye;
   an analysis part which acquires variation with time of the refractive power of the eye gazing at the fixation target at a certain presenting position within a predetermined time based on a result of measurement by the measuring optical system, and performs a frequency analysis of the acquired variation to determine spectral power of high frequency component of accommodative microfluctuation of the eye; and
   a control part which sets a meridian direction, in which the variation with time of the refractive power is acquired, to a strong principal meridian direction or a weak principal meridian direction of astigmatism when the eye is astigmatic.

4. An ocular accommodative function examination apparatus for examining an accommodative function of an examinee's eye, including:
   a fixation target presenting optical system which presents a fixation target to the eye by changing an optical distance;
   a refractive power measuring optical system which measures refractive power of the eye;
   an alignment detecting optical system which detects an alignment state of the measuring optical system with respect to the eye; and
   an analysis part which acquires variation with time of the refractive power of the eye gazing at the fixation target at a certain presenting position within a predetermined time based on a result of measurement by the measuring optical system, and performs a frequency analysis of the acquired variation to determine spectral power of high frequency component of accommodative microfluctuation of the eye, the analysis part eliminating the result of the measurement acquired while the alignment state falls outside a predetermined proper state based on a result of detection by the alignment detecting optical system.

5. The ocular accommodative function examination apparatus according to claim 4 further including a moving part which moves the measuring optical system relative to the eye so that the measuring optical system enters the proper state based on the result of detection by the alignment detecting optical system.

6. An ocular accommodative function examination apparatus for examining an accommodative function of an examinee's eye, including:

a fixation target presenting optical system which presents a fixation target to the eye by changing an optical distance;

a refractive power measuring optical system which measures refractive power of the eye; and an analysis part which acquires variation with time of the refractive power of the eye gazing at the fixation target at a certain presenting position within a predetermined time based on a result of measurement by the measuring optical system, and performs a frequency analysis of the acquired variation to determine spectral power of high frequency component of accommodative microfluctuation of the eye, the analysis part determining which of predetermined plural ranks the determined spectral power of high frequency component of accommodative microfluctuation belongs to.

7. The ocular accommodative function examination apparatus according to claim 6, wherein the analysis part acquires the variation with time of the refractive power of the eye gazing at the fixation target at each of a plurality of presenting positions within a predetermined time, and performs a frequency analysis of the acquired variation to determine spectral power of high frequency component of accommodative microfluctuation of the eye at each of the presenting positions, the analysis part making at least one of determinations as to which of the predetermined plural ranks the spectral power of high frequency component of accommodative microfluctuation at each of presenting positions belongs to and which of the predetermined plural ranks a mean of the spectral powers of high frequency component of accommodative microfluctuation at all of the presenting positions belongs to.

* * * * *